United States Patent [19]

Behrenz et al.

[11] 4,415,561
[45] Nov. 15, 1983

[54] SYNERGISTIC ARTHROPODICIDAL COMPOSITION

[75] Inventors: Wolfgang Behrenz, Overath; Manfred Schütte; Klaus Naumann, both of Leverkusen, all of Fed. Rep. of Germany

[73] Assignee: Bayer Aktiengesellschaft, Leverkusen, Fed. Rep. of Germany

[21] Appl. No.: 352,495

[22] Filed: Feb. 25, 1982

[30] Foreign Application Priority Data

Mar. 12, 1981 [DE] Fed. Rep. of Germany ....... 3109476

[51] Int. Cl.³ .................... A01N 57/00; A01N 37/00; A01N 47/10
[52] U.S. Cl. .................... 424/219; 424/305; 424/300; 424/DIG. 10
[58] Field of Search ............................. 424/219, 305

[56] References Cited

U.S. PATENT DOCUMENTS 4,183,950  1/1980  Naumann et al. .................. 424/305

FOREIGN PATENT DOCUMENTS 2658074   7/1967  Fed. Rep. of Germany .
2757769   6/1978  Fed. Rep. of Germany ...... 424/219
2913527  10/1980  Fed. Rep. of Germany ...... 424/219

*Primary Examiner*—Jerome D. Goldberg
*Assistant Examiner*—Freda Abramson
*Attorney, Agent, or Firm*—Sprung, Horn, Kramer & Woods

[57] ABSTRACT

Pesticidal compositions comprise synergistic mixtures of active compounds 1R-(—)-[(pentafluorophenyl)-methyl]-3S-3-(2,2-dichloroethenyl)-2,2-dimethylcyclopropanecarboxylate and O,O-dimethyl O-2,2-dichlorovinyl phosphate (dichlorvos) and, if appropriate, O-isopropoxyphenyl N-methylcarbamate (propoxur). These compositions may be used for combating arthropods.

7 Claims, No Drawings

SYNERGISTIC ARTHROPODICIDAL COMPOSITION

The present invention relates to new arthropodicidal synergistic combinations of the known active compounds 1R-(−)-[(pentafluorophenyl)-methyl]-3S-3-(2,2-dichloroethenyl)-2,2-dimethylcyclopropanecarboxylate and O,O-dimethyl O-2,2-dichlorovinyl phosphate (dichlorvos) and, optionally, of O-isopropoxyphenyl N-methylcarbamate (propoxur).

The invention also relates to formulations (compositions) containing these active compound combinations, their preparation and use for combating arthropods.

It is already known that propoxur and dichlorvos have a good action against insects and arachnids. These active compounds have therefore been employed with great success for many years for combating pests, particularly for combating domestic vermin. However, owing to the emergence of resistance, they suffer, like all insecticides hitherto which are in practical use, from certain losses in effect during the course of time, and these losses can, in certain cases, limit their suitability for use. The consequence of this is that, in order to combat resistant pests, the required use concentrations and use quantities have constantly to be increased in order still to obtain a satisfactory action, until, finally, the limit is reached at which the use is no longer meaningful or possible, especially for economic and application-technological reasons. The formation of resistant insect populations is particularly problematic in that their resistance is not only directed against a particular insecticide, but includes, as a rule, all active compounds of the same active-compound class, or even of several active-compound classes which are similar in their action.

The solution of the problem of developing suitable agents for combating resistant pests is therefore of particularly great importance.

The present invention now provides an arthropodicidal composition containing as active ingredients (1) 1R-(−)-[(pentafluorophenyl)-methyl]-3S-3-(2,2-dichloroethenyl)-2,2-dimethylcyclopropanecarboxylate, of the formula

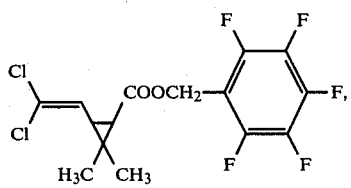

(II) O,O-dimethyl O-(2,2-dichlorovinyl) phosphate (common name: dichlorvos), of the formula

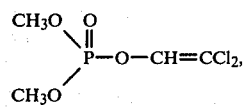

and, optionally, (III)2-isopropoxy-phenyl N-methylcarbamate (common name: propoxur), of the formula

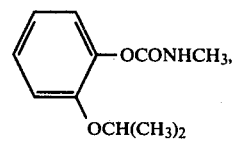

alone or in admixture with a solid or liquid or liquefied gaseous diluent or carrier.

The active-compound combinations according to this invention have a particularly powerful action against arthropods, particularly against insects and arachnids.

Accordingly, the invention also provides a method of combating arthropods (especially insects or arachnids) which comprises applying to the arthropods, or to a habitat thereof, a composition according to the present invention.

The active compounds (II) and (III) are active compounds of known commercial products, and the active compound (I) is known from German Offenlegungsschrift (German Published Specification) No. 2,658,074.

The activity of the active compound combination, according to the invention, of the two active compounds (I) and (II), or of the three active compounds (I), (II) and (III), is, surprisingly, substantially greater than the sum of the activities of the individual compounds. A genuine synergistic effect is thus present in the case of the combinations according to the invention.

The relative proportions of the active compounds can vary within relatively wide ranges in the active compound mixtures of pest-combating agents according to the invention. The proportions (parts by weight) of the two components (I) and (II) are preferably between 1:100 and 1:1, especially between 1:100 and 1:10, and those of the three components (I), (II) and (III) are preferably between 1:100:100 and 1:1:1, especially between 1:50:50 and 1:10:10. In these mixtures, the relative proportions of the components (II) and (III) can also vary within the limits given. Of course, these proportions do not have to correspond to integers.

Particularly preferred active compound mixtures or pest-combating agents are those in which the proportions (parts by weight) of the active compounds (I) and (II) are about 1:10, about 1:25 or about 1:50, and those of the active compounds (I), (II) and (III) are about 1:10:25, about 1:25:25, about 1:25:50 or about 1:50:100.

The pest-combating agents according to the invention have an excellent knock-down action and fatal action against the most diverse destructive insects and arachnids, particularly insects. In this context, the rapid knock-down action is of great importance particularly in combating domestic vermin, since the user lays particular value on a rapid elimination of the annoyance, especially for reasons of hygiene. The pest-combating agents of this invention are much more active against the pests which are resistant to carbamates, phosphoric (phosphonic) acid esters and pyrethroids, and can therefore be employed in much smaller quantities or concentrations, and with better success, than pest-combating agents which contain only 1R-(−)-[(pentafluorophenyl)-methyl]-3S-3-(2,2-dichloroethenyl)-2,2-dimethylcyclopropanecarboxylate or dichlorvos or propoxur.

The abovementioned pests include, for example, the following pests:

from the order of the Thysanura, for example *Lepisma saccharina;* from the order of the Orthoptera, for example *Blatta orientalis, Periplaneta americana, Leucophaea maderae, Blattella germanica* and *Acheta domesticus;* from the order of the Dermaptera, for example *Forficula auricularia;* from the order of the Isoptera, for example Reticulitermes spp.;

from the order of the Heteroptera, for example *Cimex lectularius, Rhodnius prolixus* and Triatoma spp.;

from the order of the Lepidoptera, for example *Ephestia kuehniella* and *Galleria mellonella;* from the order of the Coleoptera, for example *Anobium punctatum, Rhizopertha dominica, Bruchidius obtectus, Acanthoscelides obtectus, Hylotrupes bajulus, Oryzaephilus surinamensis, Sitophilus spp., Dermestes spp., Trogoderma spp., Anthrenus spp., Attagenus spp., Lyctus spp., Ptinus spp., Niptus hololeucus, Gibbium psylloides, Tribolium spp.,* and *Tenebro molitor;* from the order of the Hymenoptera, for example Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Stomoxys spp., and Tabanus spp.;

from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae,* Boophilus spp.; Rhicephalus spp., Amblyomma spp., Hyalomma spp., and Ixodes spp.

The active compound combinations can be converted into the customary formulations, such as solutions, emulsions, wettable powders, suspensions, powders, dusting agents, pastes, soluble powders, aerosols, suspension/emulsion concentrates, natural and synthetic materials impregnated with active compound, very fine capsules in polymeric substances, and formulations used with burning equipment, such as fumigating cartridges, fumigating cans, and fumigating coils, as well as ULV cold mist and hot mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

For use in baits, the formulations can contain the customary lures and baits, for example pheromones, attractive colorants, carbohydrates and proteins.

Aerosols, oil sprays and emulsion concentrates are particularly preferred formulations.

The formulations contain, in general, between 0.5 and 100% by weight of the active-compound combinations, preferably between 0.5 and 60% by weight.

The active compound combinations according to the invention may be used in the form of their formulations of the types that are commercially available or in the use forms prepared from these formulations.

The active compound content of the use forms prepared from the formulations of the types that are commercially available can vary within wide ranges. The active compound concentration of the use form can be from 0.01 to 100% by weight of total active compounds, preferably between 0.1 to 10% by weight.

The compounds may be employed in a customary manner appropriate for the use forms.

Because of their particular properties, the active compound mixtures according to the invention, or their formulations, can be employed in many areas for combating arthropods. Preferred areas of use are commercial and private hygiene (for example in schools, hospitals, foodstuff-processing factories and households), commercial and private protection of stored products (for example in foodstuff stores) and use in agriculture and animal husbandry (for example for combating stable flies).

The following examples are intended to illustrate the preparation of the pest-combating agents according to the invention.

FORMULATION EXAMPLES

EXAMPLE 1

| Spray formulation | Parts by weight |
|---|---|
| Active compound (I) | 0.01 |
| Active compound (II) | 1.0 |

-continued

| Spray formulation | Parts by weight |
|---|---|
| Methylene chloride | 5.0 |
| Deodorized kerosene/mixture or saturated aliphatic hydrocarbons | 10.0 |
| Perfume oil | 0.01 |
| Propellant: propane/butane (15:85) | 83.98 |

EXAMPLE 2

| Spray formulation | Parts by weight |
|---|---|
| Active compound (I) | 0.04 |
| Active compound (II) | 1.0 |
| Methylene chloride | 5.0 |
| Deodorized kerosene | 10.0 |
| Perfume oil | 0.01 |
| Propellant: propane/butane (15:85) | 83.95 |

EXAMPLE 3

| Spray formulation | Parts by weight |
|---|---|
| Active compound (I) | 0.04 |
| Active compound (II) | 1.0 |
| Active compound (III) | 2.0 |
| Methylene chloride | 25.0 |
| Deodorized kerosene | 12.43 |
| Perfume oil | 0.03 |
| Propellant: propane/butane (15:85) | 59.50 |

EXAMPLE 4

| Oil Spray formulation | Parts by weight |
|---|---|
| Active compound (I) | 0.08 |
| Active compound (II) | 0.5 |
| Isopropanol | 10.0 |
| Petroleum | 89.42 |

EXAMPLE 5

| Oil spray formulations | Parts by weight |
|---|---|
| Active compound (I) | 0.02 |
| Active compound (II) | 1.0 |
| Isopropanol | 10.0 |
| Petroleum | 88.98 |

EXAMPLE 6

| Oil spray formulation | Parts by weight |
|---|---|
| Active compound (I) | 0.04 |
| Active compound (II) | 1.0 |
| Active compound (III) | 1.0 |
| Isopropanol | 10.0 |
| Petroleum | 87.96 |

The following examples are intended to illustrate the activity of the active-compound combinations according to the invention.

BIOLOGICAL EXAMPLES

Spray cans or oil sprays which contained either only active compound (I) or active compound (II) or active compound (III), as well as spray cans or oil sprays which contained the active compounds (I) and (II), or the active compounds (I), (II) and (III) in combinations, were sprayed in rooms of 30 m$^3$ capacity. 3 wire cages, each containing 20 Musca domestica (♂ ♂, strain Hans) which were strongly resistant to carbamates, phosphoric (phosphonic) acid esters and pyrethroids, were previously hung in the rooms. After the application (by spraying) of 17 g of the formulations, in each case, per room, the rooms were closed and the action on the flies was continuously monitored for up to one hour. The test measured after how many minutes 50% (yields: K.D. 50 values) or 95% (yields: K.D. 95 values) of the test animals had been knocked down. The values determined are contained in the following table:

TABLE A

Musca domestica (strain Hans, ♂ ♂, multi-resistant)

| Active compounds | % (by weight) of active compounds in the formulation | Knock-down action in minutes after the application | |
|---|---|---|---|
| | | K.D. 50 | K.D. 95 |
| (I) | 0.01 to 0.08 | none | none |
| (II) | 0.5 | none | none |
| | 1.0 | 30 | 55 |
| (III) | 2.0 | none | none |
| (I) + (II) | 0.01 + 1.0 | 28 | 44 |
| (I) + (II) | 0.02 + 1.0 | 21 | 39 |
| (I) + (II) | 0.04 + 1.0 | 18 | 34 |
| (I) + (II) | 0.03 + 0.5 | 23 | 51 |
| (I) + (II) | 0.08 + 0.5 | 20 | 40 |
| (I) + (II) + (III) | 0.02 + 1.0 + 2.0 | 18 | 33 |
| (I) + (II) + (III) | 0.03 + 1.0 + 2.0 | 16 | 26 |
| (I) + (II) + (III) | 0.04 + 1.0 + 2.0 | 14 | 21 |

"None" denotes that a K.D. 50 or K.D. 95 was not achieved during the course of 1 hour.

It will be understood that the specification and examples are illustrative but not limitative of the present invention and that other embodiments within the spirit and scope of the invention will suggest themselves to those skilled in the art.

We claim:

1. An arthropodicidally active composition comprising an effective amount of (I) 1R-(−)-[(pentafluorophenyl)-methyl]-3S-3-(2,2-dichloroethenyl)-2,2-dimethylcyclopropanecarboxylate and (II) O,O-dimethyl O-(2,2-dichlorovinyl) phosphate wherein the ratio of (I):(II) is from about 1:6 to 1:50.

2. A composition according to claim 1, wherein the weight ratio of active compound (I) to (II) is from about 1:25 to 1:50.

3. A method of combating arthropods comprising applying to the arthropods, or to a habitat thereof, an arthropodicidally effective amount of a composition according to claim 1.

4. A composition according to claim 1, including (III) 2-isopropoxy-phenyl N-methylcarbamate, wherein the weight ratio of active compounds (I):(II):(III) is from about 1:10:10 to 1:50:100.

5. A composition according to claim 4, wherein (III) is present in about 50 to 100 times the weight of (I).

6. A composition according to claim 4, wherein the weight ratio of active compounds (I):(II):(III) is from about 1:25:50 to 1:50:100.

7. A method of combating arthropods comprising applying to the arthropods, or to a habitat thereof, an arthropodicidally effective amount of a composition according to claim 4.

* * * * *